United States Patent
Ying et al.

(10) Patent No.: US 10,111,787 B2
(45) Date of Patent: Oct. 30, 2018

(54) APPARATUS FOR A DIAPER, A SYSTEM, A DIAPER AND A METHOD OF MANUFACTURING AN ELECTRODE

(71) Applicant: Agency for Science, Technology and Research, Singapore (SG)

(72) Inventors: Jackie Y. Ying, Singapore (SG); Guolin Xu, Singapore (SG); Rensheng Deng, Singapore (SG); Xiaojun Chen, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 571 days.

(21) Appl. No.: 14/424,379

(22) PCT Filed: Aug. 26, 2013

(86) PCT No.: PCT/SG2013/000369
§ 371 (c)(1),
(2) Date: Feb. 26, 2015

(87) PCT Pub. No.: WO2014/035340
PCT Pub. Date: Mar. 6, 2014

(65) Prior Publication Data
US 2015/0209193 A1      Jul. 30, 2015

(30) Foreign Application Priority Data
Aug. 28, 2012   (SG) ............................... 201206388-9

(51) Int. Cl.
*G08B 21/00*        (2006.01)
*A61F 13/42*        (2006.01)
(Continued)

(52) U.S. Cl.
CPC ........ *A61F 13/42* (2013.01); *A61F 13/15707* (2013.01); *A61F 13/49* (2013.01); *A61F 2013/424* (2013.01)

(58) Field of Classification Search
CPC .... A61F 13/42; A61F 13/49; A61F 13/15707; A61F 2013/424; A61F 2013/425;
(Continued)

(56) References Cited

U.S. PATENT DOCUMENTS 3,759,246 A * 9/1973 Flack ...................... A61F 13/42
                                                                   128/886
5,036,859 A * 8/1991 Brown ...................... A61F 5/48
                                                                   128/886
(Continued)

FOREIGN PATENT DOCUMENTS

JP       2002-277435       9/2002
WO       WO-2002/016920    2/2002
(Continued)

OTHER PUBLICATIONS

"International Application No. PCT/SG2013/000369, International Search Report dated Dec. 9, 2013", (Dec. 9, 2013), 7 pgs.

*Primary Examiner* — Adnan Aziz
(74) *Attorney, Agent, or Firm* — Schwegman Lundberg & Woessner, P.A.

(57) ABSTRACT

Various embodiments provide an apparatus for a diaper. The apparatus has two electrodes and an electronic device. The electronic device is coupled to the two electrodes. The two electrodes are operable to generate a potential difference when they are electrically connected together by ionized liquid. The electronic device is operable to generate an alarm signal when the potential difference is generated. Various other embodiments relate to a corresponding system, diaper and method of manufacturing an electrode.

21 Claims, 8 Drawing Sheets

(51) Int. Cl.
*A61F 13/15* (2006.01)
*A61F 13/49* (2006.01)

(58) Field of Classification Search
CPC .. A61F 2013/15121; A61F 2013/15146; A61F 2013/15154
USPC ..................................................... 340/573.5
See application file for complete search history.

(56) References Cited

U.S. PATENT DOCUMENTS

| | | | | |
|---|---|---|---|---|
| 5,537,095 | A | * | 7/1996 | Dick ................. A61F 5/48 128/886 |
| 5,570,082 | A | * | 10/1996 | Mahgerefteh ........... A61F 13/42 340/604 |
| 5,796,345 | A | | 8/1998 | Leventis et al. |
| 6,171,289 | B1 | * | 1/2001 | Millot .................... A61F 5/443 604/336 |
| 6,433,695 | B1 | * | 8/2002 | Kai ....................... A61B 5/202 200/61.05 |
| 6,570,053 | B2 | * | 5/2003 | Roe ........................ A61F 13/42 604/361 |
| 7,352,286 | B2 | * | 4/2008 | Chan ..................... A61F 13/42 340/603 |
| 8,431,766 | B1 | * | 4/2013 | Lonero .................. A61F 13/42 604/361 |
| 8,525,673 | B2 | * | 9/2013 | Tran .................. G06F 19/3418 340/540 |
| 2002/0145525 | A1 | * | 10/2002 | Friedman ............. A61B 5/0002 340/573.5 |
| 2006/0229577 | A1 | * | 10/2006 | Roe ........................ A61F 13/42 604/361 |
| 2007/0252714 | A1 | * | 11/2007 | Rondoni ............. A61B 5/0002 340/573.5 |
| 2007/0270774 | A1 | * | 11/2007 | Bergman ................ A61F 13/42 604/361 |
| 2008/0091097 | A1 | * | 4/2008 | Linti ................... A41D 13/1281 600/389 |
| 2008/0266117 | A1 | * | 10/2008 | Song ....................... A61F 13/42 340/573.5 |
| 2008/0278336 | A1 | * | 11/2008 | Ortega .................. A61B 5/1113 340/573.5 |
| 2008/0306461 | A1 | * | 12/2008 | Jan .......................... A61F 13/42 604/361 |
| 2009/0005748 | A1 | * | 1/2009 | Ales ........................ A61F 13/42 604/361 |
| 2009/0315720 | A1 | * | 12/2009 | Clement ................. A61F 13/42 340/573.5 |
| 2009/0326493 | A1 | * | 12/2009 | Wada ..................... G01N 27/07 604/361 |
| 2010/0241094 | A1 | * | 9/2010 | Sherron .................. A61F 13/42 604/361 |
| 2011/0172625 | A1 | * | 7/2011 | Wada ..................... A61F 5/451 604/378 |
| 2012/0197224 | A1 | * | 8/2012 | Chagger ................ A61B 5/202 604/361 |
| 2012/0206265 | A1 | * | 8/2012 | Solazzo .................. A61F 13/42 340/573.5 |
| 2012/0268278 | A1 | * | 10/2012 | Lewis ..................... A61F 13/42 340/573.5 |
| 2012/0310192 | A1 | * | 12/2012 | Suzuki ................... A61F 13/42 604/361 |

FOREIGN PATENT DOCUMENTS

| | | |
|---|---|---|
| WO | WO-2011/078325 | 6/2011 |
| WO | WO-2013/013197 | 1/2013 |
| WO | WO-2014/035340 | 3/2014 |

* cited by examiner

APPARATUS FOR A DIAPER, A SYSTEM, A DIAPER AND A METHOD OF MANUFACTURING AN ELECTRODE

PRIORITY CLAIM TO RELATED APPLICATIONS

This application is a U.S. national stage application filed under 35 U.S.C. § 371 from International Application Ser. No. PCT/SG2013/000369, which was filed Aug. 26, 2013, and published as WO 2014/035340 on Mar. 6, 2014, and which claims priority to Singapore Application No. 201206388-9, filed Aug. 28, 2012, which applications and publication are incorporated by reference as if reproduced herein and made a part hereof in their entirety, and the benefit of priority of each of which is claimed herein.

FIELD OF INVENTION

Various embodiments relate generally to an apparatus for a diaper, a system, a diaper and a method of manufacturing an electrode. One specific embodiment relates to an apparatus for alerting a caregiver that it is necessary to change a diaper when it is wet.

BACKGROUND

It is a challenge for caregivers to know when to change soiled diapers for small children and some adult patients who are unable to effectively communicate the need for the change. Prolonged exposure to the soiled diaper may lead to discomfort, potential skin problems (e.g. ulcer and dermatitis), as well as infection. Therefore, alternative interventions are called for to address this problem.

One such alternative intervention is the use of a urine indicator strip which will change colour when urine is detected. However, this still requires caregivers to physically check each urine indicator strip frequently whilst the diaper is in use.

A need therefore exists to provide an apparatus which can be used to effectively alert the caregiver when it is necessary to change a diaper.

SUMMARY

Various embodiments provide an apparatus for a diaper, the apparatus comprising two electrodes; and an electronic device coupled to the two electrodes, the two electrodes being operable to generate a potential difference when electrically connected together by ionized liquid, and the electronic device being operable to generate an alarm signal when the potential difference is generated.

In an embodiment, each electrode is made of a different material.

In an embodiment, one electrode comprises a metal.

In an embodiment, one electrode comprises carbon.

In an embodiment, one electrode is rectangular or arc-shaped.

In an embodiment, the electrodes are parallel with each other.

In an embodiment, the electrodes have different lengths and/or widths.

In an embodiment, the apparatus further comprises a sheet of flexible material, wherein the electrodes are printed onto the sheet of flexible material.

In an embodiment, the electronic device comprises a speaker and the alarm signal comprises an audio signal emitted from the speaker.

In an embodiment, the electronic device comprises a light source and the alarm signal comprises a visual signal emitted from the light source.

In an embodiment, the electronic device comprises a transmitter and the alarm signal comprises a communication signal transmitted from the transmitter.

In an embodiment, the electronic device is operable to measure a value of the potential difference and cause the transmitter to transmit the communication signal in dependence on the value.

In an embodiment, the electronic device is operable to periodically measure the value of the potential difference and periodically cause the transmitter to transmit the communication signal in dependence on the value.

In an embodiment, the electronic device is operable to generate the alarm signal only when the value of potential difference is at or above a threshold value of potential difference.

In an embodiment, the apparatus comprises one or more additional electrodes, each additional electrode being coupled to the electronic device, and the electronic device being operable to generate the alarm signal when the potential difference is generated across at least two electrodes.

In an embodiment, the apparatus comprises at least two arc-shaped electrodes together forming at least a portion of a circle, and a further electrode being positioned inside the circle.

In an embodiment, the further electrode is positioned at a center of the circle.

In an embodiment, the electronic device further comprises a power source operable to provide power to generate the alarm signal.

Various embodiments provide a system, comprising an apparatus as described above; and a server having a receiver operable to receive the communication signal from the apparatus, the server being further operable to generate an indication that the communication signal has been received.

In an embodiment, the server comprises a display screen and the server is operable to display the indication on the display screen.

In an embodiment, the system comprises two or more apparatuses as described above, each apparatus being operable to include a unique identifier in a communication signal transmitted from the apparatus, the unique identifier uniquely identifying that apparatus, and wherein the server is operable to determine which apparatus transmitted a received communication signal based on the unique identifier in the received communication signal and to provide a reference to the unique identifier with the indication corresponding to the received communication signal.

Various embodiments provide a diaper comprising the apparatus as described above.

In an embodiment, the sheet of flexible material of the apparatus is a sheet of material of the diaper.

Various embodiments provide a method of manufacturing an electrode, the method comprising printing an electrode onto a sheet of material.

In an embodiment, printing comprises contacting a roller surface of a roller with the sheet of material, the roller surface being coated with ink; and moving the roller surface relative to the sheet of material to transfer ink from the roller surface to the sheet of material.

In an embodiment, the method comprises positing a layer in-between the roller surface and the sheet of material, the layer having one or more cutouts such that ink is transferred from the roller surface to the sheet of material only when a cutout is present.

BRIEF DESCRIPTION OF THE DRAWINGS

Embodiments of the invention will be better understood and readily apparent to one of ordinary skill in the art from the following written description, by way of example only, and in conjunction with the drawings, wherein like reference signs relate to like components, in which.

DETAILED DESCRIPTION

Figure 1:
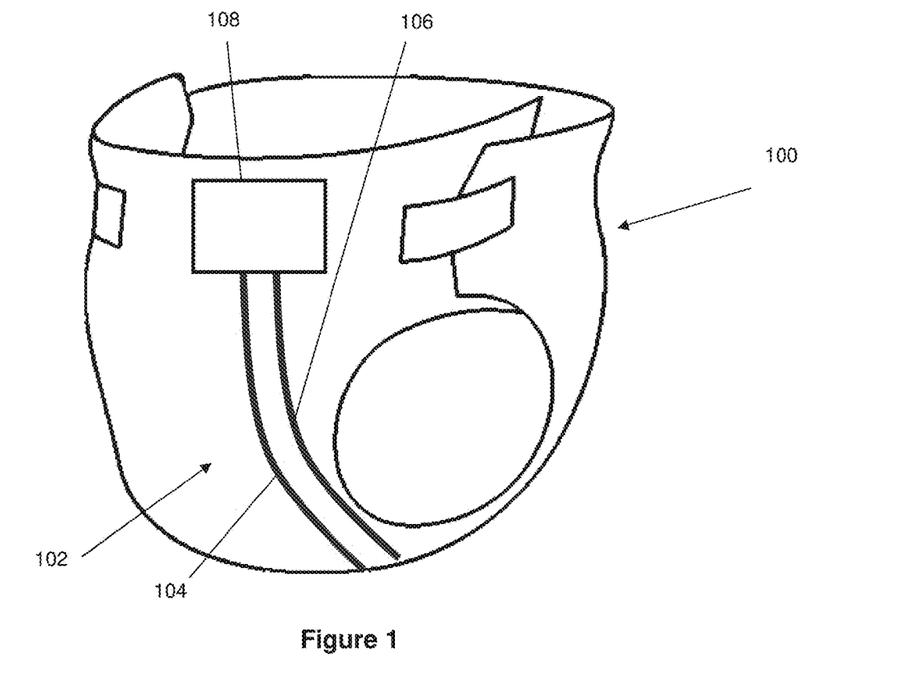
FIG. 1 shows a perspective view of an apparatus in accordance with an embodiment when located on a diaper.

With reference to FIG. 1, an apparatus (or device) 102 for a diaper 100 is shown. The apparatus 102 includes two electrodes 104 and 106. The electrodes 104 and 106 may be substantially rectangular-shaped and may be arranged on or in an exterior surface of the diaper, in close proximity to the absorption layer (not shown) of the diaper 100. In another embodiment, the electrodes 104 and 106 may be positioned on or in an internal surface or an intermediate surface of the diaper 100. The electrodes 104 and 106 may be attached to a diaper surface (e.g. by a fixture or adhesive) and/or maybe part of the surface. In an embodiment, the electrodes 104 and 106 may be printed onto a diaper surface. The two electrodes 104 and 106 are spaced apart, and are adapted to generate a potential difference when they are electrically connected together by an ionized liquid such as urine. The potential difference may be generated by a change in the material (e.g. chemical, physical and/or electrical) properties of the electrode materials as a result of the electrodes being electrically connected by liquid containing ions. Each of the two electrodes 104 and 106 is coupled to an electronic device 108. The electronic device 108 is adapted to generate an alarm signal when a potential difference is generated by or across the two electrodes 104 and 106. Accordingly, the electronic device 108 is adapted to detect when a potential difference exists across the two electrodes 104 and 106. The potential difference generated by the electrodes 104 and 106 may provide the electronic device 108 with sufficient electrical power to generate the alarm signal. In one embodiment, the electronic device 108 may be an end-user electronic device.

In an embodiment, the two electrodes 104 and 106 form a diaper wetness sensor and the electronic device 108 is a detector.

Figure 2:
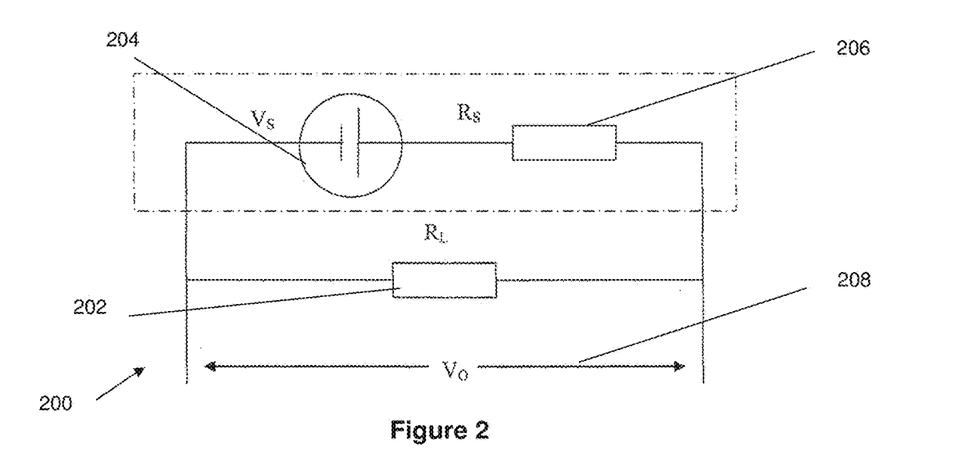
FIG. 2 shows a circuit diagram of an apparatus in accordance with an embodiment.

FIG. 2 shows an equivalent circuit of the apparatus 102 formed by electrodes 104, 106. It output a voltage $V_s$ 204. $R_s$ 206 is the internal impedance of the apparatus 102. $V_s$ 204 is the potential difference of the two electrodes 104 and 106. $R_L$ 202 which is the input impedance of the electronic device 108. $V_s$ 204 depends on the materials used to form the two electrodes 104 and 106, but is independent of the concentration of the ionized liquid. $R_s$ 206 depends on the amount (e.g. volume) of ionized liquid, the composition of the ionized liquid and the concentration (i.e. the amount of dilution) of the ionized liquid. When $R_L$ 202 is much greater than $R_s$ 206, the electronic device 108 voltage output $V_0$ 208 is almost equal to $V_s$ 204, i.e. the electronic device 108 voltage output $V_0$ 208 is independent of the $R_s$ 206 internal impedance of the electronic device 108.

In use, an ionized liquid such as urine would be present between the two electrodes 104 and 106 as the diaper 100 is used by a wearer, for example, then the wearer urinates whilst wearing the diaper 100. In this case, the ionized liquid electrically connects the two electrodes 104 and 106. In other words, the ionized liquid provides a means or channel via which charge carriers (e.g. electrons or holes) can move or flow between the electrodes 104 and 106. This flow of charge generates a potential difference between the two electrodes 104 and 106. A potential difference is generated because the two electrodes 104 and 106 are able to establish a stable voltage, in a solution of ionized liquid. For example, one electrode can be made of copper and whilst the other can be made of aluminum.

The principle of establishing a potential difference across the two electrodes 104 and 106 will now be explained. Standard redox potentials of materials at about 25° C. can be expressed as follows for 1 M of dissolved species and 1 atm of pressure.

$$\text{Half cell (positive): } Cu^{2+}+2e^-=Cu \; \varphi^0(Cu/Cu^{2+})=+0.159 \text{ V} \quad (1)$$

$$\text{Half cell (negative): } Al^{3+}+3e^-=Al \; \varphi^0(Al/Al^{3+})=-1.66 \text{ V} \quad (2)$$

$$\text{Full cell: } 2Al+3Cu^{2+}=2Al^{3+}+3Cu \quad (3)$$

The voltage difference between copper and aluminum electrodes in urine can be written as:

$$E = \varphi(Cu/Cu^{2+}) - \varphi(Al/Al^{3+}) \quad (4)$$

$$= \varphi^0(Cu/Cu^{2+}) + \frac{RT}{zF}\ln(Cu^{2+})^3 -$$

$$\varphi^0(Al/Al^{3+}) - \frac{RT}{zF}\ln(Al^{3+})^2$$

$$= E^0 - \frac{RT}{zF}\ln\frac{(\alpha_{Al^{3+}})^2}{(\alpha_{Cu^{2+}})^3}$$

where $E^0$ is the standard cell potential at the temperature of interest; $\alpha_{Al^{3+}}$ and $\alpha_{Cu^{2+}}$ are the chemical activities of $Al^{3+}$ and $Cu^{2+}$ in urine, respectively; T is the absolute temperature of the system; z is the number of moles of electrons transferred in the cell reaction; and R and F are the universal gas constant and the Faraday constant, respectively.

In the presence of a solution with ammonia e.g. urine, the negative half-cell becomes:

$$\varphi^0(Al/Al(OH)_4^-) = -2.33 \text{ V} \quad (5)$$

Hence, the output voltage of the electronic device 108 will be higher.

As shown in Equation (4), the voltage difference of the electronic device 108 depends on (i) the electrode materials, which affect the value of $E^0$, (ii) the components in urine, which affect the equilibrium of ions on the electrode surface, and (iii) the temperature.

In an embodiment, each of the two electrodes provides an opposite polarity to the other electrode. Accordingly, one electrode may be a positive electrode, whereas the other electrode may be a negative electrode. The polarity of an electrode may be determined by the material used to make the electrode. The polarity of an electrode may be determined by the material used to make the other electrode.

Figure 3:
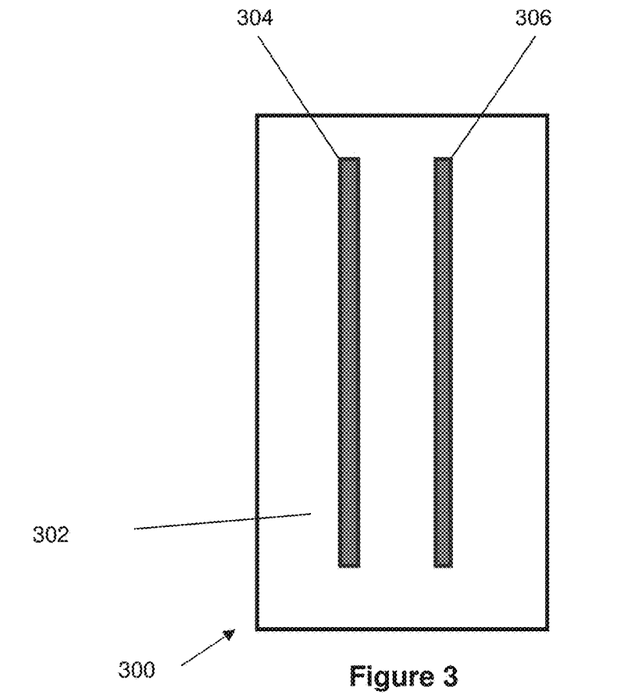
FIG. 3 shows a plan view of two electrodes in accordance with an embodiment.

FIG. 3 shows a plan view of two electrodes 304 and 306 in accordance with an embodiment. A sheet of flexible material 302 is a base (e.g. surface or substrate) on which the two electrodes 304 and 306 are fixed. For example, the electrodes 304, 306 may be printed onto the sheet 302 or stuck to, it (e.g. by an adhesive or a fastening means). Accordingly, it is to be understood that the electrons may exist on the surface of the sheet 302 and/or may penetrate the sheet 302 and form part of the body of the sheet 302. The sheet of material 302 is flexible and can be rolled up after the attachment or fixture of the two electrodes 304 and 306. The two electrodes 304 and 306 may be made of different types of materials including metals, metal oxides, electrically conductive polymers or any suitable materials that can establish a stable voltage in ionized liquid. Examples of such materials are copper, aluminum and carbon. The two electrodes 304 and 306 may be parallel to each other. The two electrodes 304 and 306 may be at an angle with each other, i.e. not parallel to each other. The two electrodes 304 and 306 may be offset from one another. One or both electrodes 304 and 306 may be partly or completely curved. One electrode may be thicker and/or longer than the other. It is to be understood that the electrodes 304 and 306 may be used in an apparatus as described above with respect to FIGS. 1 and 2, i.e. the electrodes 304 and 306 may be used with the electronic device 108 and the diaper 100. Providing the electrodes on a sheet of material provides comfort to a user of the apparatus.

Figure 4:
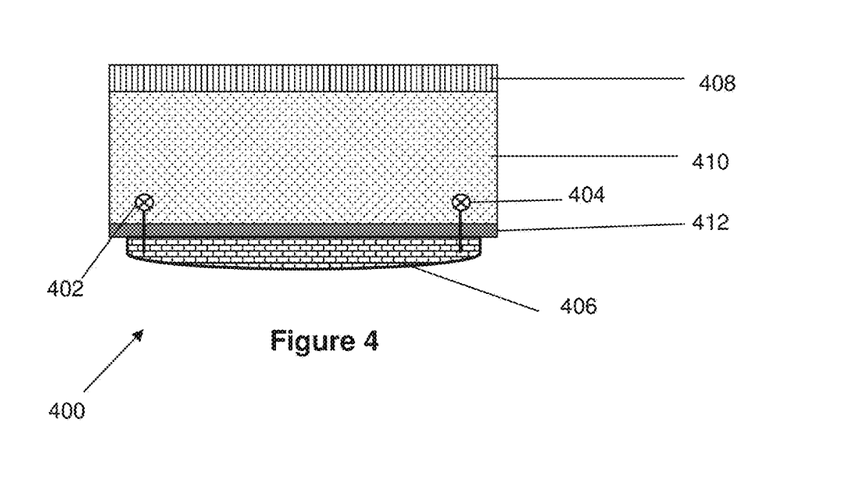
FIG. 4 shows a cross-section view of an apparatus in accordance with an embodiment.

FIG. 4 shows a cross sectional view of an apparatus 400 in accordance with an embodiment. The apparatus 400 comprises two electrodes 402, 404 coupled to an electronic device 406. As seen more particularly on FIG. 4, the apparatus 400 is fitted to a diaper, wherein the diaper comprises a urine transmission layer 408, an urine absorption layer 410, and a urine proof layer 412. Each layer may be part of a sheet of material. The urine transmission layer 408 may contact the skin of a wearer of the diaper. The urine proof layer 412 may provide an external surface of the diaper. The electronic device 406 is fixed (e.g. by a fixture or adhesive) to an outer surface of the urine proof layer 412. In this way, urine may be prevented from reaching the electronic device 406 and causing damage. The electrodes 402 and 404 penetrate through the urine proof layer 412 and into the urine absorption layer 410. In this way, the electrodes 402 and 404 are configured in use to become electrically connected by ionized liquid when sufficient urine is transferred through the urine transmission layer 408 and into the urine absorption layer 410. The potential difference generated is then provided to the electronic device 406 via the couplings (i.e. the parts which couple the electrodes 402, 404 to the electronic device 406). It is to be understood that the electrodes 402 and 404 may protrude from the electronic device (or end-user electronic device) 406 such that they can be pressed against and pierce through material layers of a diaper, such as, the urine proof layer 412 and the urine absorption layer 410. The electrodes 402 and 404 may, therefore, be protrusions. On the other hand, the electrodes 402 and 404 may be integral with one or more layers of the diaper. Accordingly, the electrodes 402 and 404 may be on a sheet of material, as described above with respect to FIG. 3. For example, the electrodes 402 and 404 may be formed with diaper layers during manufacture of the diaper. Alternatively, the electrodes 402 and 404 may be retrofitted after the diaper has been manufactured.

The electronic device 406 is adapted to generate an alarm signal on detection of the potential difference to indicate that the diaper needs changing. The position of the two electrodes 402 and 404 with respect to the various diaper layers may be adjusted to suit the potential difference required to generate an alarm signal. For example, to reduce the amount of urine required to generate an alarm signal, the electrodes 402 and 404 may be positioned further into the urine absorption layer 410, i.e. closer to the urine transmission layer 408. Alternatively, to increase the amount of urine required to generate an alarm signal, the electrodes 402 and 404 may be positioned less far into the urine absorption layer 410, i.e. closer to the urine proof layer 412. The two electrodes 402 and 404 may be made of different materials and at least one of them may include copper or aluminum. In an embodiment, one of the electrodes may be positioned further into the diaper than the other electrode. In an embodiment, the apparatus 400 may be detachable from the diaper and, possibly, re-attachable to the diaper.

Figure 5:
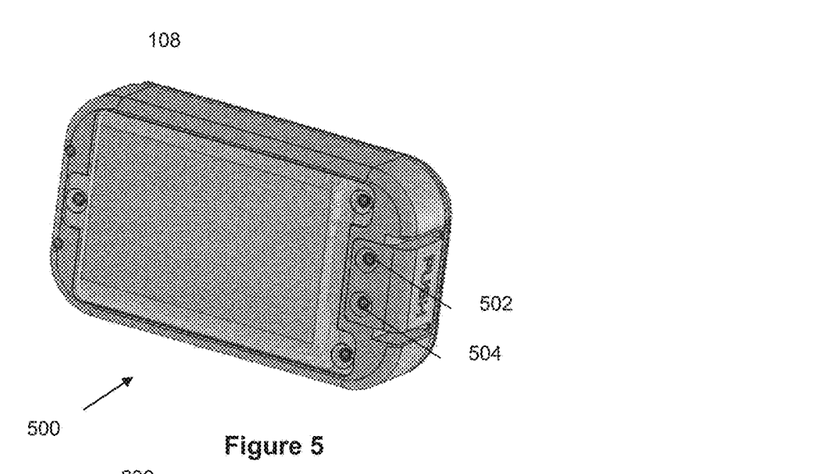
FIG. 5 shows a perspective view of an electronic device in accordance with an embodiment.

FIG. 5 shows a perspective view of an electronic device (or end-user electronic device) 500 in accordance with an embodiment. There are two connection points 502 and 504 arranged on the electronic device 500, each of these two connections points is adapted to connect to a different electrode, for example, a different one of electrodes 304 and 306 of FIG. 3. The device 500 may connect by clamping the electrodes between two surfaces so that the electrodes are mechanically and electrically coupled to the electronic device 500. Alternatively, connecting elements (e.g. cables or wires) may be used to electrically couple the electronic device 500 to the two electrodes. There may also be also a fastening means like a clip, button, hook, buckle provided on the electronic device 500 to attach the electronic device 500 to something, for example, a diaper or other piece of clothing.

The electronic device 500 may include a speaker, a light source and/or a transmitter and transmit an audio signal, visual signal and/or a communication signal, respectively. The electronic device 500 may also include a power source (not shown) for providing power to generate the alarm signal. In an embodiment, the potential difference generated by electrodes coupled to the electronic device 500 is sufficient to generate the alarm signal. In another embodiment, a power source is required to provide all or some of the voltage necessary to generate the alarm signal.

In an embodiment, the electronic device 500 is operable to measure a value of the potential difference between two electrodes and cause the transmitter to transmit a communication signal in dependence on the value of the potential difference. For example, the electronic device 500 may be configured to detect a value of potential difference within a range of values, for example, the range may be 1 to 10. 1 and 10 may represent arbitrary numbers or a specific amount of potential difference, such as, 1V and 10V or 0.1V and 1V. In this way, the electronic device ⁻30 may be able to indicate a grade or amount by which the diaper is soiled, i.e. how much it needs changing. For example, if a value of 1 is detected, this may indicate that minimal ionized liquid is present, i.e. that the diaper does not need changing. Alternatively, if a value of 10 is detected, this may indicate that a significant amount of ionized liquid is present, i.e. that the diaper needs changing. A value in-between 1 and 10 may indicate the presence of an amount of ionized liquid which is proportional to a difference between the value and both extremes (i.e. 1 and 10).

Furthermore, the electronic device 500 may be programmed with a threshold value and, if the detected value exceeds the threshold value, the communication signal is transmitted. For example, the threshold value may be 5 and, therefore, if a value of 3 is detected, a communication signal is not sent, whereas if a value of 8 is detected, a communication signal is sent. In this way, the alert signal may be generated based on an amount of ionized liquid which electrically connects the two electrodes, rather than only the presence or absence of ionized liquid In an embodiment, the electronic device 500 is adapted to periodically measure the value of the potential difference between two electrodes and cause the transmitter to periodically transmit the communication signal in dependence on the value of the potential difference. Periodic detection may limit the burden on a battery of the electronic device 500, compared to continuous detection. Periodic transmission of communication signals may also limit the burden on the battery. It is to be understood that the period by which detection is performed may be the same or different from the period by which transmission is performed.

In an embodiment, the electronic device 500 has a length of about 70 mm, a width of about 40 mm and a height of about 16 mm. In other embodiments, one or more dimensions may vary.

Figure 6:
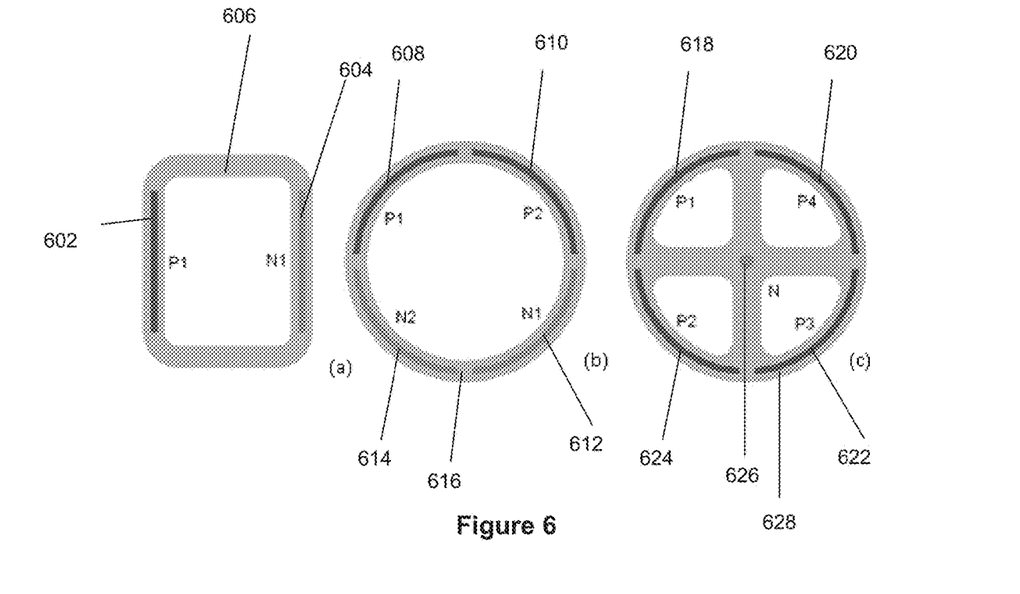
FIG. 6 shows plan views of electrode arrangements in accordance with different embodiments.

FIGS. 6(*a*) to 6(*c*) each show a plan view of an arrangement of electrodes in accordance with one of three different embodiments. In FIG. 6(*a*), the two electrodes 602 and 604 are substantially rectangular shaped and are arranged in parallel with respect to each other on a sheet of material 606. Advantageously, this provides an arrangement which is simple and inexpensive to manufacture As shown in FIG. 6 (*b*) and (*c*), there may be one or more additional electrodes to the two electrodes mentioned above. Where one or more additional electrodes are present, it is to be understood that each additional electrode may be coupled to the electronic device, and the electronic device may be operable to generate the alarm signal when the potential difference is generated across at least two electrodes (including the original two electrodes and each additional electrode).

In an embodiment, one or more electrodes are substantially arc-shaped and these electrodes may be arranged to form a circle or part of a circle, as shown in FIG. 6 (*b*) by electrodes 608, 610, 612 and 614, and in FIG. 6(*c*) by electrodes 618, 620, 622 and 624.

As seen on FIG. 6(*b*), the electrodes may comprise one or more electrode pairs. Electrodes 608 and 614 may form a first pair of electrodes and electrodes 610 and 612 may form a second pair electrodes. Each pair may include one electrode with one polarity and another electrode with the opposite polarity. Accordingly, electrodes 608 and 610 may have the same polarity. Similarly, electrodes 612 and 614 may have the same polarity.

FIG. 6 (*c*) shows arc-shaped electrodes 618, 620, 622 and 624, having the same polarity, being arranged to form a circle around an electrode 626 which is of the opposite polarity. This allows the electrodes 618, 620, 622, 624 and 626 to generate a potential difference when any pair of opposite polarity electrodes is connected together by ionized liquid. For example, electrodes 618 and 626 may generate a potential difference, or 620 and 626 may generate a potential difference.

In an embodiment different amounts of potential difference may be generated when different combinations of electrodes are connected together by ionized liquid. For example, a potential difference of 0.5V may be detected if electrodes 618 and 626 are connected together by ionized liquid and a potential difference of 1V may be detected if electrodes 618, 620 and 626 are connected together by ionized liquid. Advantageously, this provides a simple arrangement of electrodes that can be used to detect one or more specific amounts of ionized liquid, i.e. one or more specific combinations of electrodes.

In an embodiment, the material used to form each electrode may be set such that a different amount of potential difference is generated when different pairs are electrically connected together by ionized liquid. For example, when the electrodes 618 and 626 are connected together a potential difference of 0.5V may be generated; however, when the electrodes 620 and 626 are connected together by the same amount and type of ionized liquid a potential difference of 1V may be generated.

In an embodiment, the distances between different electron pairs may be different such that detection by one pair indicates the presence of more ionized liquid than detection by another pair. For example, multiple rectangular electrodes may be arranged in parallel, but one or more electrodes may have a different length and/or width to one or more other electrodes. In another embodiment, the arrangement of FIG. 6(*c*) may be used; however, the electrode 626 may not be positioned in the center of the circle formed by electrodes 618 to 624. Instead, the electrode 626 may be off center and closest to electrode 618. The next closest electrode may be 620, the next closest electrode may be 624 and the furthest electrode may be 622. Advantageously, this provides a simple arrangement of electrodes that can be used to detect one or more specific amounts of ionized liquid, i.e. one or more specific electrode pairs.

In an embodiment, the electronic device may be operable to generate the alarm signal when a potential difference is generated across any two electrodes having opposite polarities.

The arrangement and designs of the electrodes are not limited to these examples. In one example, one of the electrodes is longer that the other electrodes. The electrodes could be in the form of a metal wire, metal foil, metal strip, screen-printed metal layer or metal layer created by other means of deposition. The electrodes could be directly printed onto a diaper or be arranged to attach onto the diaper.

Various experiments were performed on an apparatus in accordance with an embodiment. In this embodiment, the apparatus 102 of FIG. 1 was used with the electron arrangement of FIG. 6(a). The following describes the results of these experiments.

Figure 7:
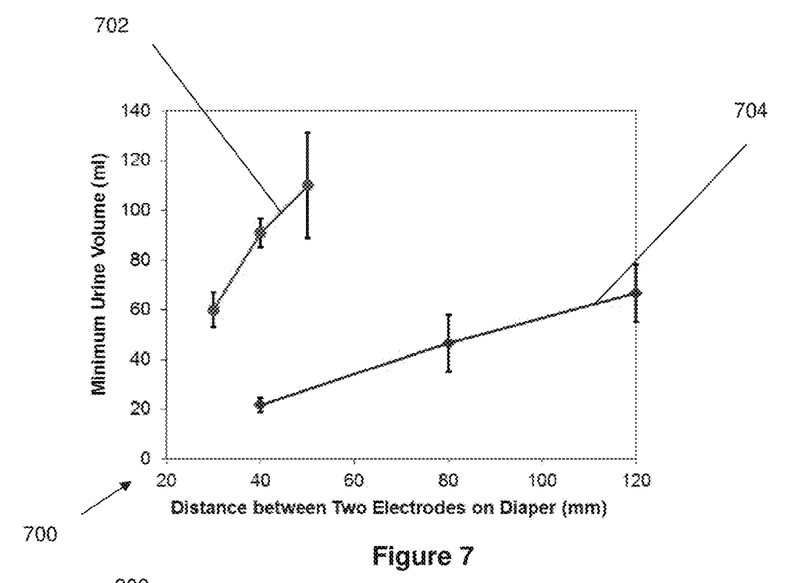
FIG. 7 shows a graphical representation of electrode separation plotted against minimum urine volume required to generate an alarm signal.

FIG. 7 is a graph of distance between the two electrodes plotted against the minimum urine volume required to generate an alarm signal. The apparatus was attached onto two types of diapers to examine the effect of the distance between the two electrodes on the minimum urine volume required for generating an alarm signal. The threshold voltage for generating an alarm signal was set at 0.4 V for Tena® adult diaper and 0.2 V for Pampers® baby (9-12 kg) diaper.

It was noted that the Pampers® diaper has a special layer above the absorption layer, which is not easily wetted, leading to a higher minimum urine volume requirement than the Tena® diaper for a given distance between electrodes, despite its lower voltage threshold setting for generating an alarm signal. Line 704 as represented by (♦) denotes the minimum amount of urine volume so as to generate the alarm signal at or above threshold voltage (0.4V) for the Tena® adult diaper; threshold voltage for wetness alarm: 0.4 V. Line 702 as represented by (•) denotes the minimum amount of urine volume so as to generate the alarm signal or above threshold voltage (0.2V) for the Pampers® baby (9-12 kg) diaper. It can be seen from FIG. 7 that a greater volume of urine is required to generate an alarm signal for the same threshold voltage as the distance between the two electrodes increases.

Figure 8:
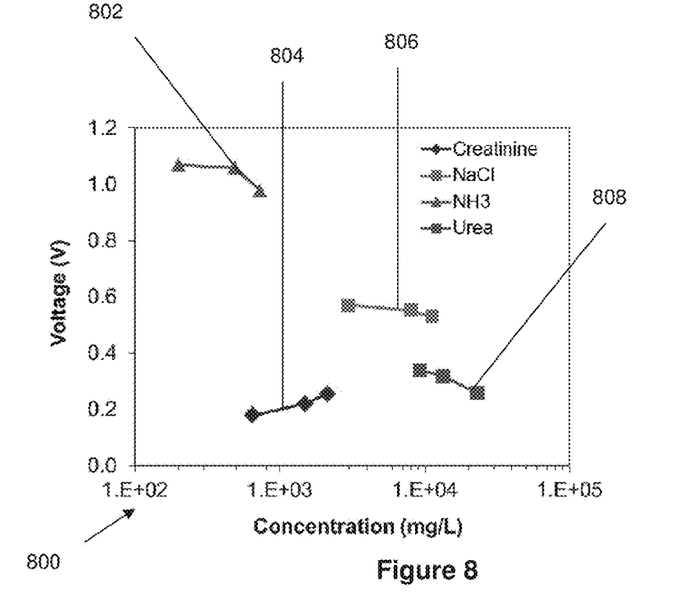
FIG. 8 shows a graphical representation of urine concentration plotted against the potential difference detected.

FIG. 8 shows a graph of concentration plotted against the potential difference detected for four different samples. Each sample includes a different component in urine namely creatinine $C_7H_4N_3O$, sodium chloride NaCl, ammonia $NH_3$, urea $CO(NH_2)_2$. Lines 802, 804, 806 and 808 represent the change in voltage for ammonia $NH_3$, creatinine $C_7H_4N_3O$, sodium chloride NaCl and urea $CO(NH_2)_2$, respectively, as the concentration of each component changes. The left, middle and right points in each curve correspond to the minimum, typical and maximum concentration of that component in urine. Ammonia solution $NH_3$ generates the highest voltage. The voltage output of the apparatus strongly depends on the urine components, and has a weak dependence on their concentrations.

Figure 9:
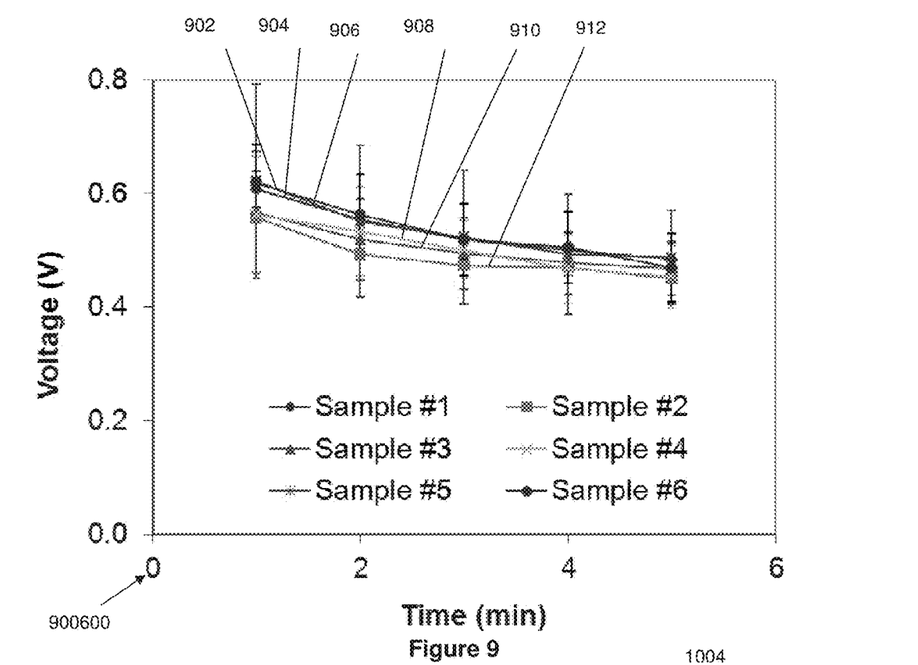
FIG. 9 shows a graphical representation of time plotted against the potential difference detected for different urine samples.

FIG. 9 shows a graph of time plotted against potential difference detected for each of six different urine samples. Lines 902, 904, 906, 908, 910 and 912 represent the change in voltage for the six different individuals. It was found that the electronic device could produce a stable voltage signal over a long period of time. Furthermore, very consistent voltage outputs were observed for the electronic device towards urine samples (Samples 1-6) from six different people, i.e. there was minimal variation of performance between difference users.

Figure 10:
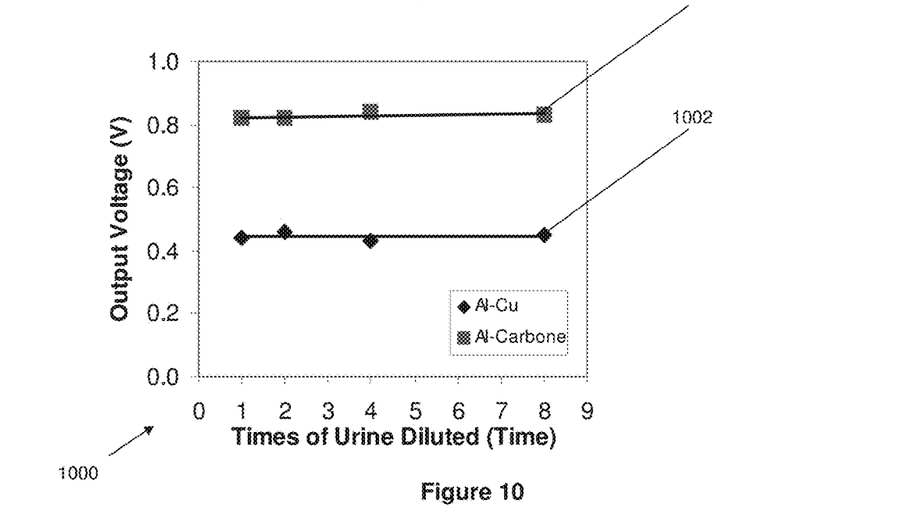
FIG. 10 shows a graphical representation of a number of times the urine sample is diluted against the potential detected by different pairs of electrodes.

FIG. 10 shows a graph of the number of times the urine sample is diluted against the potential differences detected by different pairs of electrodes. Lines 1002 and 1004 represent the change in potential difference for an aluminum/copper electrode pair and an aluminum/carbone electrode pair, respectively. The potential difference is detected by each pair of electrodes after about 5 min. It was found out that the concentration of urine has little effect on the potential difference generated by the electrodes. However, different electrode materials can result in the different output potential. For example, the output voltage from the aluminum/copper electrode pair is about 0.45V, which is lower than the output voltage from the aluminum/carbon electrode pair (0.82 V).

Figures 11, 12:
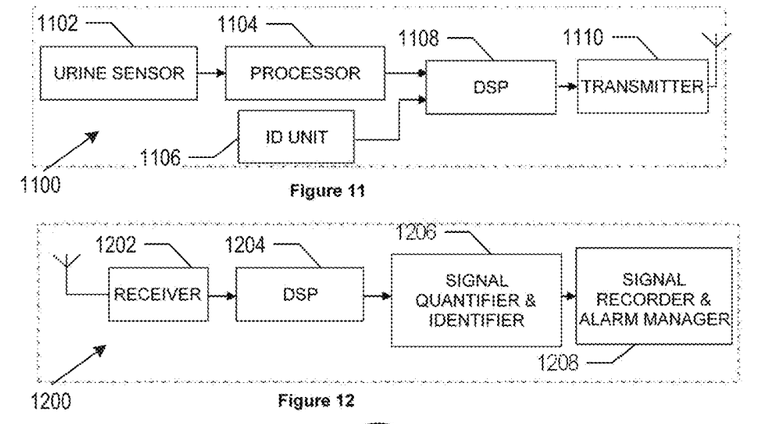
FIG. 11 shows a block diagram of an electronic device for signal transmission in accordance with an embodiment.
FIG. 12 shows a block diagram of a server for receiving signals from a plurality of electronic devices in accordance with an embodiment.

FIG. 11 shows a block diagram of an apparatus 1100 in accordance with an embodiment. The apparatus 1100 comprises a urine sensor 1102 in communication with an analogue processor 1104. The analogue processor 1104 is in communication with a digital signal processor 1108. An identification unit 1106 is also in communication with the digital signal processor 1108. The digital signal processor 1108 is in communication with a transmitter 1110.

In an embodiment, the urine sensor 1102 comprises two or more electrodes as described above. In an embodiment, the urine sensor 1102 is a pair of electrodes as described above. Accordingly, when the two or more electrodes are connected together by ionized liquid (e.g. urine), a potential difference is generated across the electrodes. The potential difference signal is passed from the urine sensor 1102 to the analog processor 1104. The analogue processor 1104 processes the potential difference signal to generate a processed signal. In an embodiment, the signal may be processed to reduce noise or amplify the signal.

The processed signal may be passed from the analog processor 1104 to the digital signal processor 1108. Additionally, an identifier of the apparatus 1100 may also be sent from the identification unit 1106 to the digital signal processor 1108. The digital signal processor 1108 may digitize the processed signal and add the identifier to the digital signal. The digital signal may then be sent by the digital signal processor 1108 to the transmitter 1110 for transmission. In an embodiment, the transmitter is a wireless transmitter and the digital signal is transmitted wirelessly. It is to be understood that the transmitted digital signal may provide the communication signal as described above in respect of other embodiments. Also, the identification unit 1106 may be absent in some embodiments or may form part of one of the other elements of the apparatus 1100. In some embodiments, the functions of one or more elements of the apparatus 1100 may be provided by the same element of one or more different elements. In an embodiment, the elements 1104 to 1110 form the electronic device as described above in respect of some other embodiments.

FIG. 12 shows a block diagram of a server 1200 in accordance with an embodiment. In one embodiment, the server 1200 is a signal receiving server system. The server 1200 comprises a receiver 1202 in communication with a digital signal processor 1204. The digital signal processor 1204 is in communication with a signal quantifier and identifier 1206. The signal quantifier and identifier 1206 is in communication with a signal recorder and alarm manager 1208.

In an embodiment, the receiver 1202 is operable to receive the communication signal (i.e. the transmitted digital signal), for example, from the apparatus 1100. In an embodiment, the receiver is a wireless receiver and the signal is received wirelessly. The received signal may then be passed by the receiver 1202 to the digital signal processor 1204 which may process the signal, for example, to eliminate noise or amplify the signal. The digital signal processor 1204 may pass the processed signal to the signal quantifier and identifier 1206, which may determine a value of potential difference included in the signal together with an identifier of the apparatus from which the received signal was transmitted. For example, the value of potential difference may be an amount of potential difference measured, e.g. 1V. Alternatively, the value may simply indicate an amount, for example, the value may be a value on a predetermined range, e.g. from 1 to 10. In an embodiment, the indication may uniquely identify a particular apparatus which generated and transmitted the received signal. For example, where the server 1200 is operating with a plurality of different apparatuses, each apparatus may include a different identifier in its signals which uniquely identifies that apparatus. Accordingly, the server 1200 can identify which apparatus sent the received signal and, therefore, which diaper needs changing. Once the value and identifier have been determined, the information is passed to the signal recorder and alarm manager 1208. The signal recorder and alarm manager 1208 may keep a record of the data received such that it records the value received against the apparatus identifier, perhaps with historical values received with the same apparatus identifier. Additionally, the signal recorder and alarm manager 1208 may generate an alarm signal (e.g. an audible and/or visual signal) if the received value indicates that the diaper attached to the apparatus needs changing. For example, this action may be triggered by comparing the received value with a threshold value and an alarm signal may be generated if the received signal is greater than the threshold value.

Alternatively, an alarm signal may be generated if a signal is received, wherein a signal is only transmitted if ionized liquid is detected.

The server 1200 may further include a display screen (not shown) for displaying an indication on the display screen. The indication may indicate that a signal has been received from a particular apparatus and/or a representation (or value) of potential difference detected by the particular apparatus. In this way, an operator of a system including the server 1200 and one or more apparatuses 1100 may monitor the display screen and determine which diapers need changing as their respective wearers use their diaper.

Figure 13:
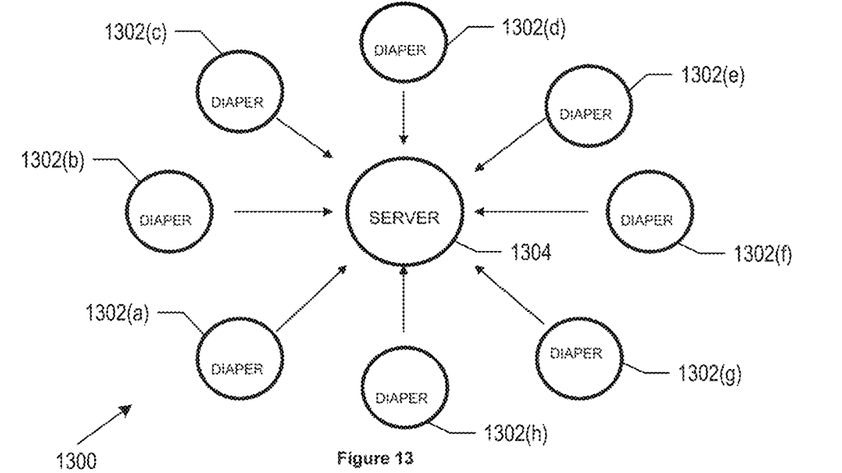
FIG. 13 shows a block diagram of a wireless signal receiver in communication with a plurality of electronic devices in accordance with an embodiment.

FIG. 13 illustrates such a system 1300 including server 1304 and apparatuses 1302(*a*) to 1302(*h*). In one embodiment, the server 1304 and the apparatuses 1302(*a*) to 1302 (*h*) are arranged in a star configuration. Each apparatus 1302 is operable to transmit a communication signal. The communication signal may include a unique identifier which uniquely identifies the apparatus from which it was transmitted. The server 1304 is operable to receive a communication signal from each of the apparatuses 1302(*a*) to 1302(*h*) and determine which apparatus transmitted the received communication signal based on the unique identifier in the communication signal. The server is operable to provide an indication to a user (e.g. via a display screen) identifying which apparatus transmitted a received signal and, therefore, which diaper needs changing. In an embodiment, the system 1300 communicates together via the ZigBee communication protocol. However, some other embodiments may use other communication protocols as will be known to a person skilled in the art.

Figure 14:
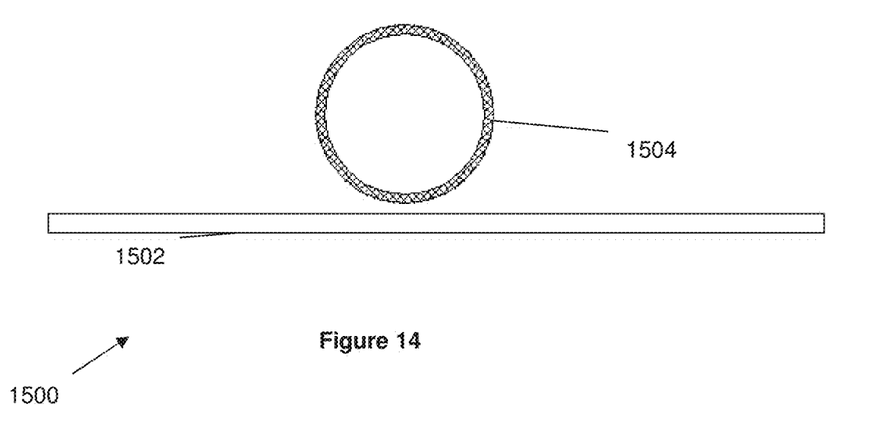
FIG. 14 shows a cross sectional view of a manufacturing step in a method of manufacturing an electrode in accordance with an embodiment.

FIG. 14 shows a cross section view of an assembly for manufacturing an electrode in accordance with an embodiment. There is a sheet of material 1502 being provided as a base. A roller 1504 is arranged to manufacture an electrode onto the sheet of material 1502.

In accordance with an embodiment, the roller 1504 is used to print an electrode or an arrangement of electrodes onto the sheet of material 1502. In an embodiment, the roller 1504 is configured to form electrodes by printing a continuous, unbroken portion (e.g. strip) of material, such as, electrically conductive ink or paint. This portion may then be cut up afterwards to form multiple electrodes. It is also understood by a person skilled in the art that the manufacturing method in accordance with an embodiment is known as rolling printing. In another embodiment, the roller 1504 is configured to form an arrangement of electrodes by forming a dashed line or strip, wherein each electrode is a separate segment of material (e.g. paint or ink) and gaps are present between each adjacent segment. As will be understood by those skilled in the art, a pattern or texture formed on the rolling surface of the roller 1504 will permit either a continuous line or a dashed line to be formed. Additionally, the size and shape of the electrodes will be controllable by changing or setting features of the pattern or texture on the roller surface.

In an embodiment, once formed, the printed electrode(s) could dry by being exposed to the atmosphere. In another embodiment, the printed electrode(s) could be exposed to pressurized air and/or heated air to accelerate the drying process. The finished product could be collected as a roll, with an electrode being printed on at least one side of the sheet of material rolled up to form the roll.

Figure 15:
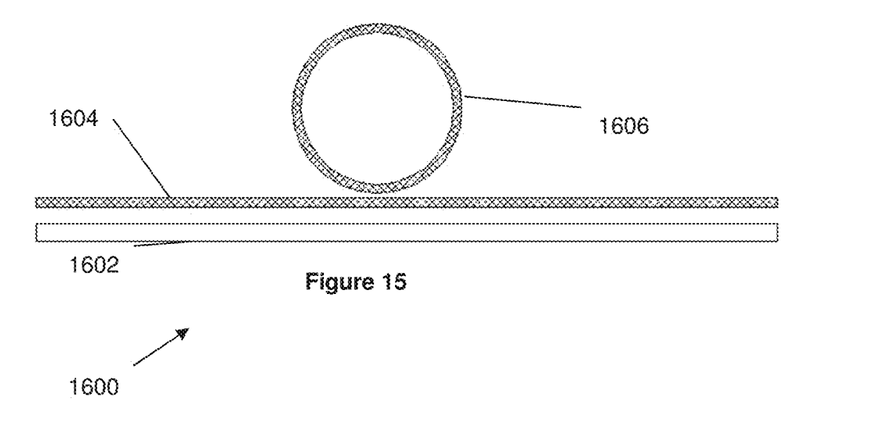
FIG. 15 shows a cross sectional view of a manufacturing step in a method of manufacturing an electrode in accordance with an embodiment.

FIG. 15 shows a cross section view of an assembly for manufacturing an electrode in accordance with an embodiment. This embodiment may be used with a silk printing process. As before, there is a sheet of material 1602 being provided as a base and a roller 1606 is arranged to form an electrode on the sheet of material 1602. However, in this embodiment, an additional layer 1604 is positioned inbetween the sheet 1602 and the roller 1606. In one embodiment, the additional layer 1604 is a mask. The additional layer 1604 may have one or more portions cut out of it and, thereby, form a stencil. The roller 1606 could have a smooth roller surface. The additional material may be made of silk.

In an embodiment, an electrode is printed onto the sheet of material 1602 by the roller 1606 only where there is a cutout in the additional layer 1604. In this way, the electrode pattern applied to the sheet 1602 is determined by the cutouts in the additional layer 1604. In a further embodiment, the roller 1606 may have a pattern or texture applied to its roller surface such that the electrode pattern applied to the sheet 1602 is a combination of the cutouts on the additional layer 1604 and the pattern or texture on the roller surface of roller 1606.

In the above-described assemblies of FIGS. 14 and 15, it is to be understood that the rollers could be rolled over a stationary sheet of material and/or the sheet of material could be moved against the roller. Therefore, it is the relative movement between the roller and the sheet of material which is important, not that one element necessarily moves whilst the other is stationary.

Figure 16:
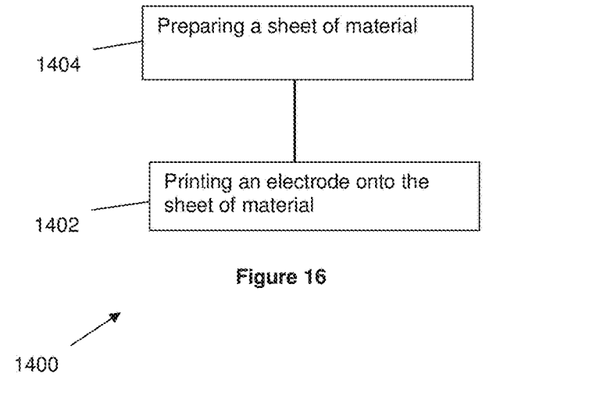
FIG. 16 shows a flowchart that illustrates a method for manufacturing an electrode in accordance with an embodiment.

FIG. 16 shows a flowchart 1400 of a method for manufacturing an electrode in accordance with an embodiment. The method provides a cost effective way to manufacture an electrode.

In step 1402, a sheet of material may be prepared. The sheet of material could be in the form of paper, natural or synthetic plastics or a portion of diaper material. In an embodiment, the sheet of material may be provided on a conveyor for moving or transporting the sheet against a roller for printing an electrode onto the sheet of material. The sheet of material may be held taut during the manufacture of the electrode. In another embodiment, the sheet of material may be looped around the roller, for example, as part of a conveyor system.

In step 1404, an electrode is printed onto the sheet of material. In accordance with an embodiment, step 1404 includes contacting a roller surface of a roller with the sheet of material to print the electrode or an arrangement of electrodes onto the sheet of material, wherein the roller surface is coated with ink. The roller may then be moved relative to the sheet of material to transfer ink from the roller surface to the sheet of material. In an embodiment, the roller may move rotationally whereas the sheet may move longitudinally. In an embodiment, step 1404 includes forming a continuous, unbroken portion (e.g. strip) of material, such as, ink or paint. This portion may then be cut up afterwards to form multiple electrodes. In another embodiment, step 1404 includes forming a dashed line or strip by a roller to form an arrangement of electrodes, wherein each electrode is a separate segment of material and gaps are present between each adjacent segment. As will be understood by those skilled in the art, a pattern or texture formed on the rolling surface of the roller will permit either a continuous line or a dashed line to be formed. Additionally, the size and shape of the electrodes will be controllable by changing or setting features of the pattern or texture on the roller surface.

In an embodiment, step 1404 includes printing the electrode by a silk printing process. As before, there is a sheet of material being provided in step 1402 and an electrode is printed onto the sheet of material as shown in step 1404. However, in this embodiment, step 1404 further includes positioning an additional layer in-between the sheet and the roller. The additional layer may have one or more portions cut out of it and, thereby, form a stencil. The electrode could be printed using a smooth roller surface. In an embodiment, the additional layer is arranged such that paint/ink is transferred from the roller surface to the sheet of material only when a cutout is present. In a further embodiment, the electrode pattern that is applied to the sheet of material is formed by a combination of the cutouts on the additional layer and a pattern or texture on the roller surface of the roller.

In an embodiment, once formed, the printed electrode(s) could dry by being exposed to the atmosphere. In another embodiment, the printed electrode(s) could be exposed to pressurized air and/or heated air to accelerate the drying process. The finished product could be collected as a roll, with an electrode being printed on at least one side of the sheet of material rolled up to form the roll.

Figure 17:
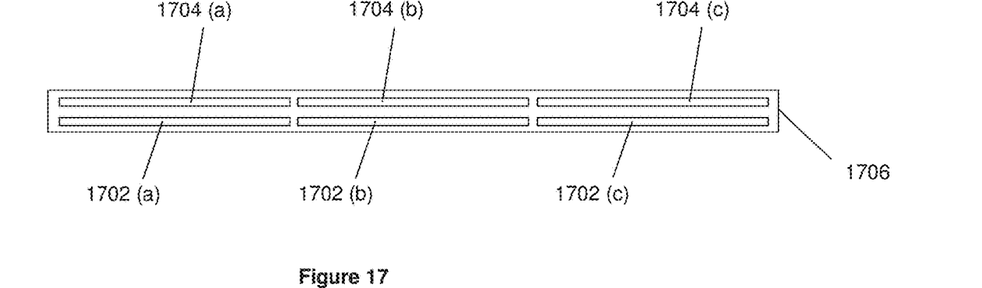
FIG. 17 shows a plan view of electrodes in accordance with an embodiment.

FIG. 17 shows a plan view of electrodes 1702 and 1704 printed onto a sheet of material 1706 in accordance with the assemblies of FIG. 14 or 15 and the method of FIG. 16. In one embodiment, there are a plurality of sets of electrodes, 1702 (*a*) to 1704(*a*). The electrodes 1702 (*a*) to 1704(*a*) are printed in a parallel pair which is segmented from an adjacent pair of electrodes 1702 (*b*) and 1704 (*b*). These two pairs of electrodes are aligned. Each electrode in each pair is separated from the other electrode in the pair by a gap. The sheet of material 1706 could be rolled up to form a roll. Advantageously, the roll could be provided to a caregiver for use in an apparatus as described above in the above embodiments. For example, a portion of the roll may be torn off to provide an electron pair for use with an electronic device, such as, the electronic device 500. In an example, the roll may also be provided with perforations which cause the roll to tear in-between adjacent electron pairs. Once torn off, the detached electron pair may be attached to an electronic device and a diaper. For example, the electron pair may be positioned and fixed against an outside surface of the diaper, an inside surface of the diaper or in-between two surfaces of the diaper.

However, those skilled in the art will realize that many other methods could be used so long as they attach or print an electrode onto the sheet of material.

It is known to use a urine indicator strip which will change colour when urine is detected. However, this still requires caregivers to physically check each urine indicator strip frequently whilst the diaper is in use. Checking is inconvenient, especially if there is more than one individual for whom the caregiver is responsible. However, an advantage of the above-described embodiments is that an alarm signal is generated which alerts the caregiver without requiring laborious checking. For example, the alert signal can be an audible alarm. Therefore, the caregiver does not need to visually inspect each diaper and, instead, can wait for an alarm then go and replace the diaper from which the alarm was generated.

It is an advantage of the above-described embodiments that the alarm signal is generated based on potential difference being measured. This is advantageous because, as shown above, potential difference is not dependent on urine concentration. Alternatively, a system which measured capacitance and/or conductance in the electrodes, rather than potential difference, would be less effective because both capacitance and conductance are more dependent on urine concentration. Therefore, the amount of urine which is required to generate an alarm signal would fluctuate in dependence on the user and, even, how hydrated the user is.

According to the above-described embodiments, a potential difference is generated and detected when the two electrodes are electrically connected together by ionized liquid. This potential difference is then used to generate an alarm signal. Those skilled in the art will realize that many other arrangements or types of electrodes or electronic devices could be used so long as they generate a potential difference and alarm signal in the presence of ionized liquid.

In an embodiment, the electronic device is a wireless device. The wireless device may comprise a processor module, an input module such as a keypad and an output module such as a display. The above-described functions of the electronic device may be implemented as software, such as a computer program being executed within the wireless device.

The processor module may be connected to a wireless network via a suitable transceiver device, to enable wireless communication and/or access to e.g. the Internet or other network systems such as Local Area Network (LAN), Wireless Personal Area Network (WPAN) or Wide Area Network (WAN).

The processor module may include a processor, a Random Access Memory (RAM) and a Read Only Memory (ROM). The processor module may also include a number of Input/Output (I/O) interfaces, for example an I/O interface to the display, and an I/O interface to the keypad.

The components of the processor module may communicate via an interconnected bus and in a manner known to the person skilled in the relevant art.

The computer program may be supplied to the user of the wireless device encoded on a data storage medium such as a flash memory module or memory card/stick and read utilising a corresponding memory reader-writer of a data storage device of the wireless device. The computer program is read and controlled in its execution by the processor. Intermediate storage of program data may be accomplished using RAM.

While several exemplary embodiments have been presented in the foregoing detailed description of the invention, it should be appreciated that a vast number of variations exist, including variations as to the arrangement of the electrodes and the electronic device and how the detection of potential difference is carried out.

It is to be understood that one or more features from one of the above-described embodiments may be combined with one or more features from one or more other above-described embodiments to form different embodiments which fall within the scope of the appended claims.

It will be appreciated by a person skilled in the art that numerous variations and/or modifications may be made to the present invention as shown in the specific embodiments without departing from the scope of the appended claims as broadly described. The present embodiments are, therefore, to be considered in all respects to be illustrative and not restrictive.

The invention claimed is:

1. An apparatus for a diaper, the apparatus comprising:
a plurality of electrodes; and
an electronic device coupled to at least two electrodes of the plurality of electrodes;
the at least two electrodes of the plurality of electrodes being operable to generate a potential difference when electrically connected together by ionized liquid, and the electronic device being operable to generate an alarm signal when the potential difference is generated, wherein the plurality of electrodes comprise at least two arc-shaped electrodes together forming at least a portion of a circle, and a further electrode being positioned inside the circle.

2. The apparatus of claim 1, wherein the further electrode is positioned at a center of the circle.

3. The apparatus according to claim 1 wherein the electronic device further comprises a power source operable to provide power to generate the alarm signal.

4. The apparatus according to claim 1 wherein each electrode of the at least two electrodes is made of a different material.

5. The apparatus according to claim 1 wherein one electrode of the at least two electrodes comprises a metal.

6. The apparatus according to claim 1 wherein one electrode of the at least two electrodes comprises carbon.

7. The apparatus according to claim 1 wherein the at least two electrodes are parallel with each other.

8. The apparatus according to claim 1 wherein the at least two electrodes have different lengths and/or widths.

9. The apparatus according to claim 1 further comprising a sheet of flexible material, wherein the at least two electrodes are printed onto the sheet of flexible material.

10. The apparatus according to claim 1 wherein the electronic device comprises a speaker and the alarm signal comprises an audio signal emitted from the speaker.

11. The apparatus according to claim 1 wherein the electronic device comprises a light source and the alarm signal comprises a visual signal emitted from the light source.

12. The apparatus according to claim 1 wherein the electronic device comprises a transmitter and the alarm signal comprises a communication signal transmitted from the transmitter.

13. The apparatus according to claim 12, wherein the electronic device is operable to measure a value of the potential difference and cause the transmitter to transmit the communication signal in dependence on the value.

14. The apparatus according to claim 13, wherein the electronic device is operable to periodically measure the value of the potential difference and periodically cause the transmitter to transmit the communication signal in dependence on the value.

15. The apparatus according to claim 13, wherein the electronic device is operable to generate the alarm signal only when the value of the potential difference is at or above a threshold value of the potential difference.

16. The apparatus according to claim 1 wherein the apparatus comprises one or more additional electrodes, each additional electrode being coupled to the electronic device, and the electronic device being operable to generate the alarm signal when the potential difference is generated across at least two electrodes.

17. A system comprising:
an apparatus for a diaper, the apparatus comprising:
two electrodes; and
an electronic device coupled to the two electrodes;
the two electrodes being operable to generate a potential difference when electrically connected together by ionized liquid, and the electronic device being operable to generate an alarm signal when the potential difference is generated, wherein the two electrodes are arc-shaped forming at least a portion of a circle, and a further electrode is positioned inside the circle, wherein the electronic device being operable to generate the alarm signal when the potential difference is generated across at least one of the two arc-shaped electrodes and the further electrode; and
a server having a receiver operable to receive a communication signal from the apparatus, the server being further operable to generate an indication that the communication signal has been received.

18. The system of claim 17, wherein the server comprises a display screen and the server is operable to display the indication on the display screen.

19. The system of claim 17, comprising:
two or more of the apparatuses, each apparatus being operable to include a unique identifier in a communication signal transmitted from the apparatus, the unique identifier uniquely identifying that apparatus, and
wherein the server is operable to determine which apparatus transmitted a received communication signal based on the unique identifier in the received communication signal and to provide a reference to the unique identifier with the indication corresponding to the received communication signal.

20. A diaper comprising:
two electrodes; and
an electronic device coupled to the two electrodes;
the two electrodes being operable to generate a potential difference when electrically connected together by ionized liquid, and the electronic device being operable to generate an alarm signal when the potential difference is generated, wherein the two electrodes are arc-shaped forming at least a portion of a circle, and a further electrode is positioned inside the circle, wherein the electronic device being operable to generate the alarm signal when the potential difference is generated across at least one of the two arc-shaped electrodes and the further electrode.

21. The diaper of claim 20, further comprising a sheet of flexible material, wherein the electrodes are printed onto the sheet of flexible material, wherein the sheet of flexible material is a sheet of material of the diaper.

* * * * *